United States Patent [19]

Weiss et al.

[11] 4,122,587
[45] Oct. 31, 1978

[54] PATIENT SECURING DEVICE

[75] Inventors: Karl Weiss, Erlangen-Buckenhof; Helmut Rost, Erlangen, both of Germany

[73] Assignee: Siemens Aktiengesellschaft, Berlin & Munich, Germany

[21] Appl. No.: 771,447

[22] Filed: Feb. 24, 1977

[30] Foreign Application Priority Data

Mar. 15, 1976 [DE] Fed. Rep. of Germany ....... 2610830

[51] Int. Cl.² .............................................. A61F 5/37
[52] U.S. Cl. .................................. 128/134; 105/477; 280/179 A; 269/328; 254/56; 254/79; 254/164; 254/169; 248/499
[58] Field of Search ...................... 128/134, 133, 352; 105/477; 280/179 A; 269/328; 254/71, 79, 164, 161, 169, 56; 248/499

[56] References Cited

U.S. PATENT DOCUMENTS

| 2,487,425 | 11/1949 | Collins | 128/352 |
| 2,692,600 | 10/1954 | Curyea | 128/352 |
| 3,981,492 | 9/1976 | Hallman | 269/328 |

Primary Examiner—Henry J. Recla
Attorney, Agent, or Firm—Hill, Gross, Simpson, Van Santen, Steadman, Chiara & Simpson

[57] ABSTRACT

A hold-down device particularly for use in securing patients to examination tables and the like. The device includes mounting member for attachment to opposite sides of the examination table, one of the mounting members having first and second actuatable take-up drums controlled by a rachet connected handle, a belt is past from the first take-up drum across the patient to the other holder and around a free wheeling roll in that holder and back across the patient to the second take-up drum. The rolls are geared such that the second take-up drum revolves three times faster than the first take-up drum.

14 Claims, 4 Drawing Figures

PATIENT SECURING DEVICE

BACKGROUND OF THE INVENTION

1. Field of the Invention

This invention relates to patient securing devices and more particularly to tensionable belt patient securing devices.

2. Prior Art

Hold-down devices for securing and restricting movement of patients on X-ray tables and other examination tables are known to the art. Such devices include hold-downs utilizing belts or straps which pass from a tension device across the patient to a belt attachment means are also known. One such device utilizes a belt which has one end secured to a holder which can be attached to a profiled side rail of the examination table. The other end of the belt is wound on a take-up drum supported in a holder which can be attached to the opposite profiled side of the support table. The take-up drum is provided with a rachet by which the belt can be tautly stretched across a patient positioned between the two holders.

However, in devices such as that above described, the tensioning device has a noticeable disadvantage in that as the belt is drawn in the direction in the take-up drum at the time of securing the patient, movement of the belt across the patient will cause lateral shift of the patient in the direction of the take-up drum. This not only leads to an unpleasant friction or rubbing of the belt against the patient, who may be unclothed, but also creates a lateral shift of surface adjacent internal body parts. As a result organ displacement can occur and this displacement will therefore result in a distorted picture on a florescent screen or X-ray photograph.

Another form of known patient securing device utilizes take-up holders wherein both ends of the belt are secured to separate take-up drums, each of which can be rachet actuated. With this type of a hold-down, lateral shifting of the patient can be avoided if the rachets are evenly tightened on both sides of the patient, since one take-up drum must be located on each side of the patient. In order for this to occur either two persons are necessary, acting in sequence, one on each take-up device, or the physician or other personnel must repeatedly go from one side of the examination table to the other in order to alternately operate first one and then the other take-up.

It would therefore be an advance in the art to provide a strap hold-down device for patient examination tables and the like where the hold-down could be tensioned from one side of the table without imposing a lateral shift on the patient.

SUMMARY OF THE INVENTION

It is therefore a principal object of this invention to provide a patient hold-down device including a tensioning system which prevents lateral shifting of the patient under influence of the hold-down device when the hold-down belt is tightened and which can be easily operated by one person from one side of the patient examination table.

As disclosed herein this invention provides a first mounting member or holder which is attachable to the examination table and which carries a freewheeling roller. A second holder, attachable to the examination table on the opposite side, carries two take-up drums which are parallel positioned, generally one above the other. The opposed ends of the belt are attached to the drums, and the drums are coupled via a gear unit having a ratio of 1 to 3. The drums can be secured in a locked position by means of a releasable rachet system.

In the disclosed embodiment, the belt extends from a first one of the take-up drums across the examination table and around the freewheeling roller, back across the examination table and is attached to a second of the take-up drums. In the disclosed embodiment, the first drum to which the first stretch of the belt, i.e., that stretch of the belt which is the shortest from patient contact to the drum, is associated with the slower gearing. By this means, when a patient is secured to the examination table by the belt, the belt portion which lies directly on the patient will be drawn in equally from both sides of the examination table. Thus friction and pull on the patient is avoided. In this manner surface adjacent organs will no longer be displaced or laterally shifted.

In a preferred embodiment of the invention, a spring loaded locking pawl is attached to the holder which carries the two drums and is engageable with a rachet wheel to lock the same against rotation. A pin carried by a rotatable hand grip member can be rotated around the rachet wheel and brought into and out of contact with the locking pawl to release the same. A rachet pawl carried by the rotatable hand grip is likewise engageable with the rachet wheel and with a stationary release pin carried by the holder, engagement with the stationary pin lifting the rachet pawl from the rachet wheel. By properly circumferentially spacing the pawls and pins around the rachet wheel, it can be provided that a back and forth movement of the hand grip will tension the belts while a simple backward rotation of the hand grip past a certain point will cause a complete release of the belt tension allowing release of the patient.

By providing a rachet pawl which is spring loaded into contact with the rachet wheel, and by providing a holder carried pin which is engageable with the rachet pawl to disengage it from the rachet wheel upon movement of the hand grip to a given circumferential point in a direction reverse the tensioning direction, and by properly spacing the positioning of the rachet pawl release pin with respect to the positioning of the locking pawl release, it is possible to provide a hand grip swing range of between 20° to 90° during which the rachet wheel will be out of engagement with the rachet pawl while the rachet wheel is still prevented from freewheeling in the release direction by the locking pawl. In this manner, influence of the hand grip can be removed from the rachet wheel for a portion of the swing range of the hand grip without disengaging the locking pawl. Of course the rachet wheel will totally freewheel when out of engagement with the locking pawl, but will be allowed to freewheel without influence of the hand grip, in a tensioning direction during that portion of the swing range between the point where the rachet pawl release pin engages the rachet pawl and that point where the locking pawl release pin engages the locking pawl. By thus providing for freewheeling of the rachet wheel in the tensioning direction, it is possible to quickly rotate the take-up drums by means of a drive other than the hand grip, such as a knob attached to one of the drums, without emparting movement to the hand grip and without the rachet pawl providing a drag.

Also illustrated in the disclosed embodiment is a simplified method of attaching the holders to the examination table. The holders are provided with at least one reverse bend attachment clamp which is matable with a reverse bend side rail molding on the edges of the examination table in an overlap condition therewith. By designing the holders so that they can be pivoted in one direction to clear the overlap, the holders can then be attached to the examination table sides at any point along the length of the examination table without having to index the clamps and table sides at one end of the examination table and thereafter slide the holders along the length to the desired point. This allows the holders to be easily attached at a desired point irrespective of the fact that other holders or mounting devices, such as leg supports, I.V. stands, and the like may have already been clamped to the examination table edge rails at points along the length of the table. A spring biased pressure bar can be provided to resist tilting of the holders from the clamped to the unclamped positions.

It is therefore an object of this invention to provide a patient hold-down strap tightening mechanism which does not impose a lateral shift on the patient during tensioning.

It is another more particular object of this invention to provide a patient hold-down system for examination tables wherein a strap extends between a holder device located at one side of the table across the patient and around a freewheeling roller held in a holder device located at the opposite side of the patient and back again across the patient to the first holder, the first mentioned holder being equipped with drive rollers with one end of the belt attached to each drive roller, and the drive rollers being geared together and revolving at different speeds.

It is another object of this invention to provide a novel rachet drive for a double roller patient hold-down belt tensioning device, the rachet device including a locking pawl releasable by movement of a hand wheel in a direction opposite to a tensioning direction movement of the hand wheel, the hand wheel being equipped with a tensioning rachet pawl.

Other objects, features and advantages of the invention will be readily apparent from the following description of a preferred embodiment thereof, taken in conjunction with the accompanying drawings, although variations and modifications may be effected without departing from the spirit and scope of the novel concepts of the disclosure, and in which:

DESCRIPTION OF THE PREFERRED EMBODIMENTS

Figure 1:
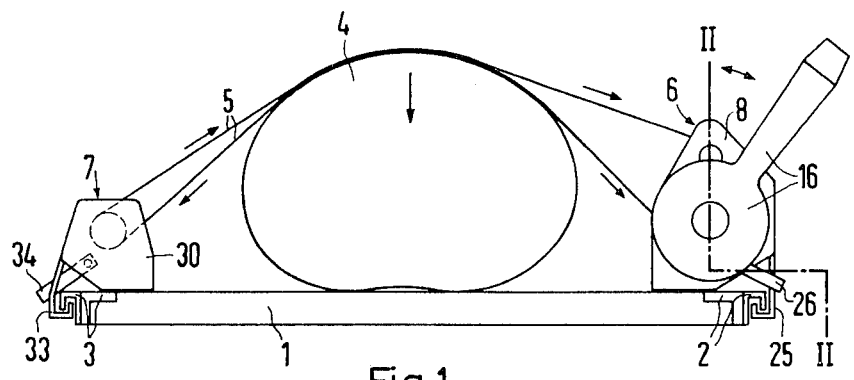
FIG. 1 is a diagrammatic cross-sectional view through a patient lying on an examination table, the table equipped with the patient hold-down of this invention.

FIG. 1 illustrates a patient examination table 1 or like patient supporting member which has profiled side rails 2 and 3 which form a groove open at the bottom which run along the length of the sides of the examination table 1. A patient 4 is illustrated as resting on the support table. A hold-down or securing device includes a strap or belt 5 which passes across the patient on top of the patient between the sides of the examination table and securely holds the patient in place on the table. The belt 5 is attached at both sides of the examination table to holders 6 and 7. The holders are affixed to the side rails 2 and 3.

Figure 2:
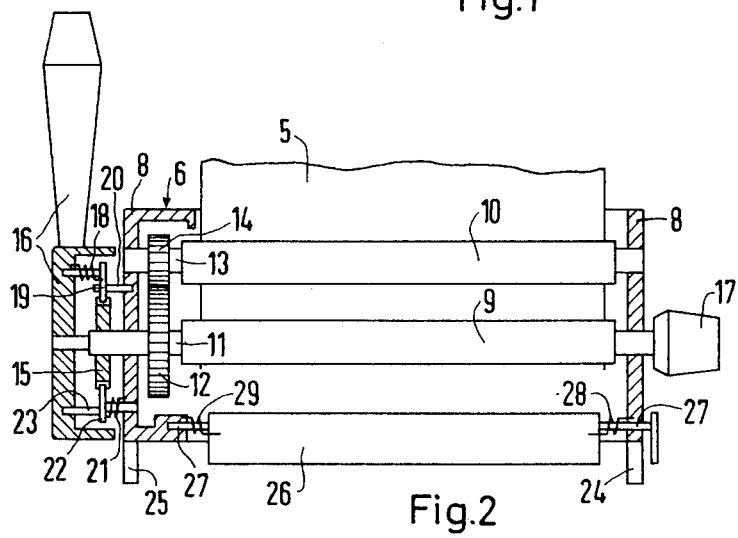
FIG. 2 is a cross-sectional view taken along the lines II—II of FIG. 1.

The holder illustrated on the right hand side of FIG. 1 is shown in FIG. 2 in section and includes a housing member 8 which has two take-up drums 9 and 10 carried therein. The drums are, in the illustrated embodiment, positioned one above the other and are parallel. The axle 11 of the lower drum 9 has a gear wheel 12 attached thereto at one end of the drum. A gear wheel 12 attached to an axle 13 of the upper take-in drum adjacent one end of the upper take-in drum meshes with the gear wheel 12. The gear wheel 12 and the gear wheel 14 are dimensioned such that the gear wheel 14, and therefore the upper take-up drum 10, makes three times as many revolutions per unit of time as the gear wheel 12 and the lower take-up drum 9 connected to the gear wheel 12.

The axle 11 of the lower take-up drum extends beyond the gear wheel 12 and through a journal mount in the housing wall to a position exterior of the housing where a rachet wheel 15 is mounted on the axle 11.

Next to the rachet wheel, 15, on the same axle 11, a hand grip 16 is attached, outboard of the rachet wheel from the housing 8. The hand grip is freely rotatable on the axle 11.

The opposite end of the axle 11 is journaled through the opposite side of the housing 8 and is equipped with a hand knob 17 which is non-rotatably attached to the axle. The rotation of the knob 17 will cause rotation of the lower drum 9 whereas rotation of the hand grip 16 does not necessarily cause rotation of the lower drum 9.

Figure 3:
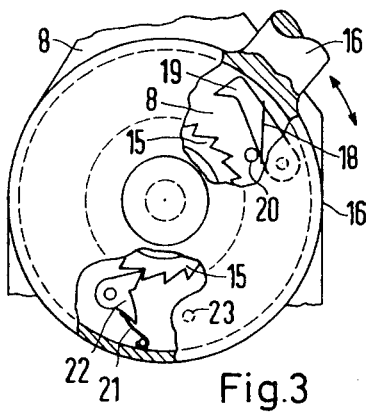
FIG. 3 is a partially sectional fragmentary view of the rachet drive system of this invention.

FIG. 3 illustrates the hand grip drive to the drum 9. A rachet pawl carried by the hand grip 16 is urged against the rachet wheel 15 by means of spring 18. The spring is mounted on the hand grip 16 surrounding an axle shaft for the rachet pawl 19. A pin 20 fixedly attached to the wall of the housing 8 projects outwardly towards the hand grip into the area radially outwardly of the rachet wheel and in a position where it can abut the rachet pawl 19.

Additionally, a locking pawl 22 is attached to the housing wall 8 by means of an axle shaft. A spring 21 received around the axle shaft of the locking pawl urges the locking pawl into engagement with the rachet wheel at a point circumferentially spaced from the pin 20. The locking pawl 22, when in engagement with the rachet wheel, prevents reverse or untensioning movement of the drum 9 by preventing such movement of the rachet wheel 15. A pin 23 attached to the hand grip 16 projects towards the housing wall 8 and into an area radially outwardly of the rachet wheel 15 where it is contactable with the locking pawl 22. The pin 23 is spaced circumferentially from the rachet pawl 19.

The housing 8 is attached to the examination table by means of fastener extensions 24 and 25. These fastener extensions have a configuration mating with the profiled side rails 2 and 3 and they define a groove open to the top which can then overlap the groove of the profiled side rails which are open to the bottom with short legs of the rail projecting into the groove of the extensions 24, 25 and short legs of extensions 24, 25 projecting into the grooves of the rails 2 and 3.

In the plane immediately above the extensions 24, 25, and preferably extending substantially the length of the housing 8, a pressure bar 26 is attached to the housing. The pressure bar is rotatable with respect to the housing 8 around an axle 27 which is aligned parallel to the take-up drums. The pressure bar is spring urged via springs 28 and 29 into engagement with the top of the rail 2 to resist outboard tilting of the holder 6 with respect to the examination table thereby maintaining the engagement between the side rails and the extensions 24 and 25.

Figure 4:
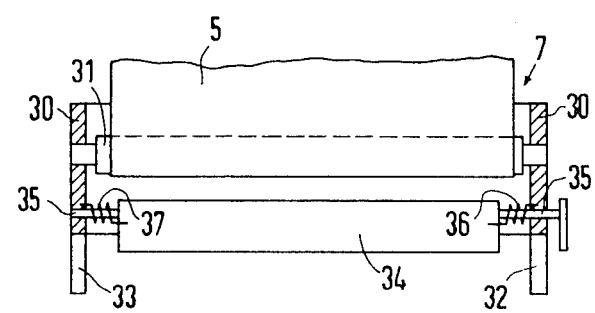
FIG. 4 is a partially sectional view of the freewheeling roller holder of this invention.

The holder 7, shown on the left hand side of FIG. 1, and illustrated in cross-section in FIG. 4 includes a housing member 30 which carries a roller 31 mounted on an axle which is journaled in side walls of the housing 30 for freewheeling with respect to the housing. The belt 5 is past around the freewheeling roller 31. Additionally, as described in connection with holder 6, the holder 7 includes extensions 32, 33 which are designed to mate with the side rail 3 of the examination table 1. In the plane immediately above the extensions, pressure bar 34 is mounted on axle 35 and engaged by springs 36 and 37 to maintain engagement between the extensions 32, 33 and the side rail 3 the same as pressure bar 26 described in connection with holder 6. The freewheeling roller 31, when the housing 7 is attached to the side of the examination table opposite the holder 6 will lie parallel to the drums 8 and 9.

OPERATION OF THE DEVICE

When a patient resting on the examination table 1 is to be secured with the device of this invention, the holder 7 with roller 31 is attached to the side rail 3 by means of the extensions 32, 33 on the side of the examination table which is the least accessible. In order to attach the holder 7, it is necessary that the holder be tilted outboard with respect to the examination table. A lever on the end of axle 35 can release pressure of the pressure bar 34 to facilitate this and thereafter, with the holder 7 mounted, the pressure bar will resist outboard tilting of the holder 7 so as to prevent disengagement. Thus the pressure bar 34 will be pressed against the side rail to keep the mounting 7 in position even without tension having been applied to the belt 5.

In a like manner, the holder 6 which carries the hand grip 16, and take-up drums 9 and 10 for the belt is inserted on the opposite, or more easily accessible side of the examination table. Holder 6 will also be pressed against its associated examination table side rail by means of the pressure bar 26.

With the free ends of the belt attached respectively to drums 9 and 10, and the belt passed around roller 31, the belt can be quickly moved to a patient engaging position by means of the hand knob 17. As soon as the belt 5 rests against the patient, the desired tension can be applied by rotating hand grip 16 counterclockwise as shown in FIG. 3 to a point where the rachet pawl 19 is moved out of engagement with the pin 20 which is attached to housing 8 of the holder 6. At that point the spring 18 will engage the rachet pawl 19 with the rachet wheel in a further counterclockwise rotation of the hand grip 16 will cause rotation of the rachet wheel 15 and thus of the take-up drums 9 and 10. Clockwise rotation of the hand grip 16 will cause the pawl 19 to slide over the rachet wheel. During clockwise rotation of the hand grip, locking pawl 22 carried by the housing 8 of the holder 6 will engage the rachet wheel under influence of spring 21 and prevent tension release of the belt by preventing back rotation of the drums 9 and 10. Thus by a back and forth motion of the hand grip, it is possible to tension the belt 5 to the desired point.

If however it is desired to release tension, the hand grip 16 is taken back further in a clockwise direction, the rachet pawl 19 will then engage pin 20 and will thereby lift it out of engagement with the rachet wheel. Upon a further clockwise movement of the hand grip, pin 23 attached to the hand grip will engage locking pawl 22 releasing contact between the locking pawl and the rachet wheel 15. In this manner the take-up drums 9 and 10 are made freewheeling. By making the drums 9 and 10 freewheeling, tension will be instantly withdrawn from the belt and the patient can be released.

During take-up of the belt on the drums 9 and 10, both ends of the belt are simultaneously wound around the drums, counterclockwise on the bottom drum and clockwise on the more rapidly rotating top drum 10. Opposite rotation is caused by the gearing 12, 14. By means of the differential take-up of the belt, the top leg of the belt 5, which is furtherest away from the examination table 1 will be taken up so rapidly, in relation to the bottom portion of the belt in contact with the patient and connected to take-up drum 9 that it will also take-up the lower belt around the freewheeling roller 31. Thus the portion of the belt that is in contact with the patient and closest to the examination table 1 will be drawn in equally from both sides of the patient both around drum 9 and, via roller 31, around drum 10. This equalized take-up of both sides of the lower portion of the belt means that the lower portion will have a component of force in the direction of the arrow indicated in FIG. 1 perpendicular to the examination table. Thus the lower portion of the belt will not impose any lateral shift on the patient. Since the upper portion of the belt is not in contact with the patient, but rides over the lower portion of the belt, it will not impose lateral shift on the patient.

It can therefore be seen from the above that this invention provides a novel hold-down device for securing a patient to an examination table by means of a belt which passes from a take-up holder across the patient to an opposite side of the examination table thence around a freewheeling roller and back across the patient to the take-up holder.

The take-up holder is equipped with parallel drums with one end of the belt attached to each drum and the drums are geared together such that they revolve at different speeds in a manner which will cause the stretch of the belt in contact with the patient to be drawn towards both sides of the examination table simultaneously thus giving it a force component perpendicular to the examination table.

A novel rachet connection for the actuation of the tensioning drums is also disclosed.

Although the teachings of our invention have herein been discussed with reference to specific theories and embodiments, it is to be understood that these are by way of illustration only and that others may wish to utilize our invention in different designs or application.

We claim as our invention:

1. In a device for securing a patient to an examination table including an examination table, a belt for extending between the sides of the table over the top of the table and holder mechanisms including base means attached to the table adjacent each side thereof with the belt passing between the holder mechanisms, and means for tensioning the belt, the improvement of one of the holders being equipped with a freewheeling roller around which the belt passes, and a second holder having a slower revolvable take-up drum and a faster revolvable take-up drum mounted therein in parallel relationship to one another, said slower revolvable drum being mounted closest to said base means opposite ends of the belt being attached one end respectively to one drum and the other end respectively to the other drum, the belt passing around the freewheeling roller, selectively actuatable means or revolving the drums simultaneously including gear means on each drum for revolving the drums together at different relative rotational speeds whereby, the belt, when passed around the freewheeling roller having a lower stretch extending from a slower revolving drum across the examination table, closest to the surface of the examination table and another stretch passing across the examination table above the first mentioned stretch the other stretch attached to a faster revolving drum.

2. A device according to claim 1 wherein the drums are geared together with the gears having a ratio of 1 to 3.

3. A device according to claim 1 wherein the selectively actuatable means comprises a releasable one way drive rachet mounted on said second holder including a rotatable rachet wheel operatively connected to one of the drums, a drive member rotatably mounted relative to said rachet wheel, a rachet pawl pivotally mounted on said drive member in alignment with said rachet wheel for driving said rachet wheel, spring means biasing the rachet pawl into driving engagement with the rachet wheel, whereby, rotation of said drive member in one direction causes said rachet pawl to engage said rachet wheel and revolve said drums.

4. The device according to claim 4 wherein the rachet wheel has associated therewith a spring loaded locking pawl pivotally mounted on said second holder in an aligned position relative to said rachet wheel, spring means biasing said locking pawl into locking engagement with the rachet wheel, a release mechanism for said locking pawl, said release mechanism including a first projection mounted on the drive member in radial alignment with said locking pawl and a second projection mounted on the second holder in radial alignment with said rachet pawl, the drive member and first projection being revolvable with respect to the locking pawl, whereby the projections are engageable with the locking pawl and rachet pawl upon rotation of the drive member to pivot the locking pawl and rachet pawl against the respective spring means and out of contact with the rachet wheel.

5. The device of claim 4 wherein the rachet pawl rotates the rachet wheel upon movement of the drive member in a first direction and the first and second projections engage the locking pawl and rachet pawl to release the same upon movement of the drive member in a second direction opposite the first direction.

6. The device of claim 5 wherein the rachet pawl and the second projection are dimensioned with respect to one another and spaced from one another such that engagement of the second projection with the rachet pawl maintains the rachet pawl out of engagement with the rachet wheel over a swing range of the drive member of between 10° and 90° rotation in the second direction from a point of initial engagement of the second projection with the rachet pawl.

7. The device according to claim 1 wherein the examination table has shaped side rails running along side edges thereof and the base means of said holders have mating shaped extensions thereon engageable with the shaped side rails to removably attach the holders to the examination table, the mating of the extensions and the side rails providing an overlapping connection between the extensions and side rails limiting movement of the holders in at least one direction with respect to the table.

8. A device according to claim 7 wherein the holders are equipped with spring urged pressure bars biased into contact with portions of the table by biasing means, said bars resisting movement of the holders, when attached to the examination table, in a second direction with respect to the table, movement of the holders in the second direction being required to release the overlapping connection of the extensions and the side rails.

9. The method of securing a patient to an examination table which comprises the steps of placing a patient on the examination table, attaching holder mechanisms to opposite sides of the examination table, passing a belt between said holders with a first stretch of the belt passing from a tension holder across the patient and in engagement therewith to a freewheeling roller carried by the other of said holders, a second stretch of the belt extending from the freewheeling roller across the said patient on top of the first stretch to the said tension holder, attaching opposite free ends of the belt to rotatable take-up drums in said tension holder, gearing the take-up drums such that one of the drums rotates faster than the other of the drums, securing the end of the belt associated with the first stretch to the slower of the take-up drums, attaching the end of the belt associated with the second stretch to the faster of the take-up drums, and rotating said drums in opposite directions whereby both ends of the belt will be wrapped around their respective take-up drums at different rates of speed such that the stretch of belt in contact with the patient will be drawn simultaneously towards both sides of the examination table in a manner to produce a compressive force on the patient which is substantially perpendicular to the examination table.

10. A tensioning holder for use in association with patient securing systems comprising a housing member, a pair of take-up drums rotatably mounted in said housing member, said take-up drums positioned in parallel relation to one another, a patient holddown web extending between said drums and having ends attached to the drums, gear means gearing said take-up drums together for simultaneous rotation, said gear means having a ratio of other than 1 to 1 whereby one of said take-up drums will be revolved slower than the other of said take-up drums, a shaft extension on one of said take-up drums, a rachet wheel affixed to said shaft for rotation therewith, a hand grip rotatably mounted on said shaft in spaced relation to said rachet wheel, a rachet pawl carried by said hand grip, spring means urging the rachet pawl into contact with the rachet wheel, the rachet pawl having a driving face opposed to a driven face on the rachet wheel when in contact with the wheel, the rachet pawl being pivotable on said hand grip whereby movement of the hand grip in a first circumferential direction will drive the rachet wheel and its associated shaft in said first direction by engagement with the rachet pawl.

11. The device according to claim 10 wherein a locking pawl is pivotally mounted on said housing, spring means urging said locking pawl into abutting engagement with the rachet wheel and causing the locking pawl to effectively resist rotation of the rachet wheel in a direction contrary to the first direction of rotation of the rachet wheel caused by the rachet pawl, a first projection on said hand grip in radial alignment with the locking pawl a second projection mounted on the housing in radial alignment with said rachet pawl whereby upon movement of the hand grip in a direction opposite the first direction, engagement of the first and second projections with the locking pawl and rachet pawl, respectively, will effectively pivot the locking pawl and rachet pawl against their respective spring means to release the locking pawl and rachet pawl from abutting engagement with the rachet wheel.

12. A device according to claim 11 wherein the rachet pawl, locking pawl and projections are spaced circumferentially such that movement of the hand grip in the direction opposite the first direction will first cause disengagement of the rachet pawl with the rachet wheel and second, upon further movement in the direction opposite the first direction, will release the locking pawl.

13. A device according to claim 12 wherein the further movement is between 10° and 90° of revolution of the hand grip on the axle.

14. A device according to claim 13 wherein the axle is equipped with a non-rotatably carried second hand grip.

* * * * *